United States Patent [19]
Thompson et al.

[11] Patent Number: 5,545,517
[45] Date of Patent: Aug. 13, 1996

[54] SELECTIVE METAL ION DETECTION USING A PHOTOLUMINESCENT INDICATOR BINDING TO A MACROMOLECULE-METAL ION COMPLEX

[75] Inventors: Richard B. Thompson, Baltimore, Md.; Eric R. Jones, Honolulu, Hi.

[73] Assignee: The United States of America as represented by the Secretary of the Navy, Washington, D.C.

[21] Appl. No.: 213,409

[22] Filed: Mar. 15, 1994

[51] Int. Cl.$^6$ ............................ C12Q 1/00; G01N 21/00
[52] U.S. Cl. ................... 435/4; 435/18; 435/808; 436/73; 436/164; 436/172; 436/805; 422/55; 422/82.7; 422/82.8; 422/82.11; 356/73.1; 356/301
[58] Field of Search .................... 435/4, 18, 808; 436/73, 164, 172, 805; 422/55, 82.07, 82.08, 82.11; 356/73.1, 221, 218, 301

[56] References Cited

U.S. PATENT DOCUMENTS 5,141,312  8/1992  Thompson et al. .................... 356/218

OTHER PUBLICATIONS

Chen et al, *The Journal of Biological Chemistry*, vol. 242, No. 24, pp. 5813–5823, 1967.
Thompson et al, *Anal. Chem.*, vol. 65, No. 7, pp. 853–856, 1993.
James et al, *Chemical Abstracts*, vol. 92, pp. 647, Ref. #31841d, 1980.
Lieberman et al, *Chemical Abstracts*, vol. 107, pp. 423–424, Ref. #204814f, 1987.
Liberman et al, *Chemical Abstracts*, vol. 114, pp. 907–908, Ref. #198618w, 1991.
Thompson et al., "Component Selection for Fiber–Optic Fluorometry", Applied Spectroscopy 44 (1) 117–22 (1990).
Szmacinski et al., "Optical measurements of pH using fluorescence Lifetimes and phase–modulation fluorometry", Analytical Chem. 65 (13) 1668–74 (1993).
Thompson et al., "Phase Fluorimetric Method for Determination of Standard Lifetimes", Analytical Chem. 60 (7) 670–74 (1988).
Thompson et al., "Enzyme–based Fiber Optic Zinc Biosensor", Analytical Chem. 65 (6) 730–34 (1993).

Thompson et al., "Fiber Optic pH Sensor Based on Phase Fluorescence Lifetimes", Analytical Chem. 65 (7) 853–56 (1993).
Golden et al., "Fluorometer and tapered fiber optic probes for sensing in the evanescent wave", Optical Eng'g 31 (7) 1458–62 (1992).
Lakowicz et al., "Frequency–domain fluorescence spectroscopy", in *Topics in Flourescence Spectroscopy vol. 1: Techniques*, (J.R. Lakowicz, ed.) pp. 293–336 (Plenum Press 1991).
Thompson, "Flourescence–Based Fiber Optic Sensors", in *Topics in Flourescence Spectroscopy vol. 2: Principles* (J.R. Lakowicz, ed.) pp. 345–365 (plenum Press 1991).
Bruland, "Complexation of zinc by natural organic ligands in the central North Pacific", Limnology and Oceanography 34 (2) 269–85 (1989).
Sherrell et al., "Zinc, chromium, vanadium and iron in the Mediterranean Sea", Deep–Sea Research, 35 (8) 1319–34 (1988).

*Primary Examiner*—Christina Y. Chan
*Assistant Examiner*—Abdel A. Mohamed
*Attorney, Agent, or Firm*—Thomas E. McDonnell; John J. Karasek

[57] ABSTRACT

The present invention is a process and apparatus for metal ion detection. The process of the invention has the steps of (1) disposing, in an analyte medium, a macromolecule suitable for selective complexation with the target metal ion species; (2) disposing, in the analyte medium, an appropriate photoluminescent indicator that will emit in a measurably different manner when bound to the metallomacromolecule complex, compared with its unbound state; (3) exciting the photoluminescent indicator species; and (4) monitoring the emission of the photoluminescent indicator species to detect changes in its emission. The apparatus of the invention has (1) a macromolecule suitable for selective complexation with the target metal ion species disposed in an analyte medium; (2) an appropriate photoluminescent indicator that will emit in a measurably different manner when bound to the metallomacromolecule complex, compared with its unbound state, also disposed in the analyte medium; (3) a source for exciting the photoluminescent indicator species; and (4) a detector for monitoring the emission of the photoluminescent indicator species to detect changes in its emission.

6 Claims, 6 Drawing Sheets

2-(3 METHOXY-4 ETHOXYPHENYL)-4-CHLOROQUINOLINE-6-SULFONAMIDE

N-(1-ANTHRACENYL)-4-SULFONAMIDO-BENZENE-SULFONAMIDE

ETHYL-2-(4-SULFONAMIDEPHENYL)-4-HYDROXYQUINOLINE-6-CARBOXYLATE

N-N(N'-(4'SULFAMOYLGLUTARANILYAMIDOETHYL)-4-AMINO-3,6-DISULFO-1,8-NAPHTHALIMIDE

FIG. 10

SELECTIVE METAL ION DETECTION USING A PHOTOLUMINESCENT INDICATOR BINDING TO A MACROMOLECULE-METAL ION COMPLEX

BACKGROUND OF THE INVENTION

1. Field of the Invention

The present invention related to the selective detection of metal ions in solution or other analyte medium, and more particularly to a fiber optic-based real time, continuous process and apparatus for the highly selective detection of metal ions at nanomolar concentrations.

2. Description of the Related Art

Fiber optic chemical sensors are devices of growing importance in fields as diverse as oceanography, chemical process control, in vivo clinical diagnosis, and environmental monitoring. Fiber optic sensors have the capability of continuously monitoring the level of an analyte in a sample that may be up to kilometers away from the instrument, or in an inaccessible space. A large fraction of these sensors exploit a change in photoluminescence (e.g., fluorescence) in response to the analyte as a means to transduce its presence or level. Fluorescence-based sensing, and more generally photoluminescence-based sensing, is desirable due to its high sensitivity, good selectivity, and relatively straightforward instrumentation.

A very important potential application of fiber optic chemical sensors is in the field of chemical oceanography. One of the current issues in chemical oceanography is the difficulty of determining certain chemical constituents of seawater, such as trace metals, at many points in the ocean. The basis of the problem is the slow rate at which discrete samples can be obtained from deep in the water column and analyzed, usually by preconcentration followed by atomic absorption or emission spectrophotometry, or electrochemical methods. Such techniques permit analysis of only a few dozen samples per day because they cannot usually be stored, the analyses require skilled labor, and moreover the sophisticated instrumentation necessary is ill-suited to shipboard operation. The rate and ease of measurement are important issues in designing data collection efforts to understand phenomena occurring on a large scale, such as global climate change, especially given the high cost ($10,000 per day) and limited availability of ships where such analytical chemistry may be performed.

For example, it is of particular interest to monitor zinc (II) concentrations in seawater. Zn(II) is one of a group of metal ions (along with Fe and Mn) having particular importance because they serve as nutrients, and indeed are required as enzyme cofactors by many taxa of organisms for survival. These ions typically exhibit a concentration dependence with depth characteristic of nutrients (low levels in the photic zone where most plankton are, then increasing to a constant level at greater depths).

The difficulties of quantitatively analyzing Zn(II) in seawater exemplify many of the practical problems encountered with remote, real time quantitative analysis of environmental metal ions. Much Zn(II) is dissolved in the form of complexes with ill-defined organic ligands, such that free concentrations of these ions are typically in the subnanomolar range. Indeed, there are large regions of the ocean where low concentrations of one or more of these ions are believed to limit primary productivity of microorganisms. Zinc(II) levels in sea water have only recently been measured with accuracy, because of the great difficulty of avoiding contamination of the samples during collection and subsequent analysis. Stripping voltammetry has been the method of choice, with some effort being devoted to understanding the speciation of zinc ion in the ocean.

Other metal ions of interest as analytes include cobalt, copper, lead, mercury, cadmium, and nickel.

For trace metal analyses in sea water, the classical fluorimetric indicators such as morin or hydroxyquinoline sulfonate that have been incorporated into fiber optic sensors are ill-suited mainly because they are insufficiently selective. Even the excellent chelatometric indicators for calcium do not discriminate against similar concentrations of Zn or Mn when these are present, nor Mg at hundred-fold higher concentrations. By comparison, an indicator for Zn in sea water must exhibit million-fold (60 dB) selectivity with respect to magnesium, as well as other cations. Such selectivity is not to be found in typical synthetic chelators such as these, or ionophores. However, some metalloenzymes exhibit exceptional binding selectivity for the metal ions which participate as cofactors in catalysis. An example of this is the carbonic anhydrase from mammalian erythrocytes (carbonate hydro-lyase, E.C. 4.2.1.1), which functions in vivo by dehydrating bicarbonate to give $CO_2$ (and vice versa), only the latter of which can pass through cell membranes.

A continuously monitoring in situ sensor would be desirable for these studies since it could be maintained at a desired depth and continuously report analyte levels as the ship proceeded along its course. Fiber optic chemical sensors have precisely these qualities, and recognizing these advantages Wait, Lieberman, and others have described fiber optic chemical sensors for use at sea.

SUMMARY OF THE INVENTION

Accordingly, it is an object of this invention to provide real-time, continuous, highly selective quantitative analysis of metal ions using photoluminescence.

It is a further object of this invention to provide this analysis for nanomolar target species in an environment with many potential interferents (such as in vivo or in seawater).

It is a further object of this invention to provide this analysis in situ, obviating the need for preconcentration and/or storage of samples.

It is a further object of this invention to provide this analysis with compact, rugged equipment suitable for field (e.g., shipboard) use.

These and additional objects of the invention are accomplished by the structures and processes hereinafter described.

The present invention is a process and apparatus for metal ion detection. The process of the invention has the steps of (1) disposing, in an analyte medium, a macromolecule suitable for selective complexation with the target metal ion species; (2) disposing, in the analyte medium, an appropriate photoluminescent indicator that will emit in a measurably different manner when bound to the metallomacromolecule complex, compared with its unbound state; (3) exciting the photoluminescent indicator species; and (4) monitoring the emission of the photoluminescent indicator species to detect changes in its emission.

The apparatus of the invention has (1) a macromolecule suitable for selective complexation with the target metal ion species disposed in an analyte medium; (2) an appropriate photoluminescent indicator that will emit in a measurably different manner when bound to the metallomacromolecule complex, compared with its unbound state, also disposed in the analyte medium; (3) means for exciting the photoluminescent indicator species; and (4) means for monitoring the emission of the photoluminescent indicator species to detect changes in its emission.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DETAILED DESCRIPTION OF THE PREFERRED EMBODIMENTS

Figure 1:
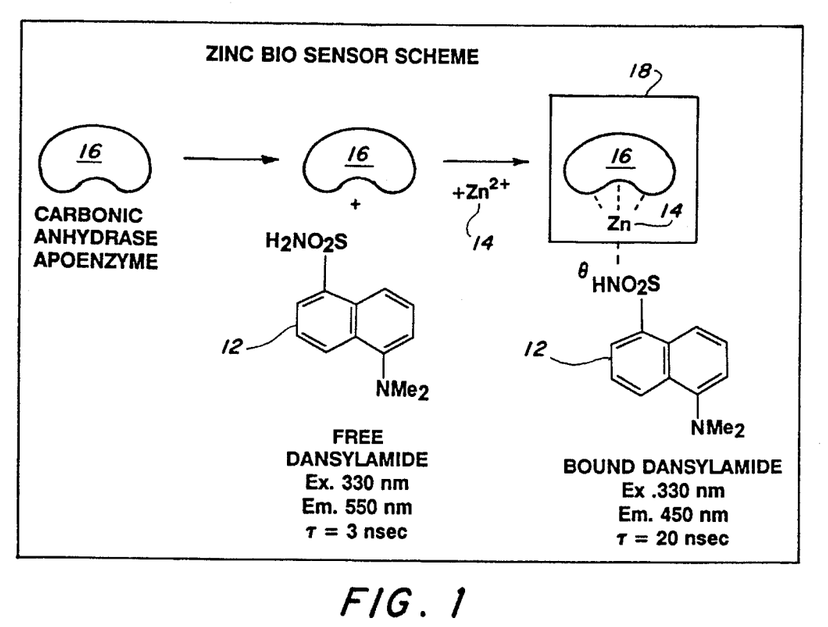
FIG. 1 shows the transduction scheme for the invention.

The present invention encompasses a wide variety of preferred embodiments. What is common to all of the embodiments of the invention is a common transductive mode, wherein a photoluminescent species 12 exhibits one photoluminescent response while free in the analyte medium (i.e., while not bound to a complex 18 of the target metal ion 14 and a selective binding macromolecule 16), and a measurably different photoluminescent response when bound to a complex 18 of the target metal ion 14 and a selective binding macromolecule 16.

Skilled practitioners will recognize that many photoluminescent indicator species 12 exhibit different types of variable photoluminescent responses in their bound and unbound states. Photoluminescent indicator species 12 are known to vary, inter alia, in their lifetimes, in the location of $\lambda_{max}$ (i.e., in the photoluminescent peak wavelength), in their emission polarization, in their emission anisotropy, and in the ratio of intensities for two or more emission peaks. Apparatus are known for measuring each of these photoluminescent responses.

For example, apparatus are know for measuring the ratio of intensity of two selected photoluminescent peaks. Likewise, photoluminescent lifetime may be measured in the time domain, typically by time correlated single photon counting. Photoluminescent lifetime also may be measured in the frequency domain, typically by phase modulation fluorometry. Skilled practitioners will recognize that lifetime measurement has several desirable features. Recently, Wolfbeis, Lakowicz, and others have emphasized the virtues of fluorescence sensing based on changes in fluorescence lifetime due to the chemical analyte. In addition to having most of the advantages of the ratiometric approach, lifetime-based sensing has two further benefits. First, it is more flexible in that several means may be used. to transduce the level of a chemical as a change in lifetime. Second, the dynamic range of a sensor based on equilibrium binding is (in favorable cases) much larger than expected. Szmacinski and Lakowicz demonstrated one case where a pH indicator undergoing a single ionization event permitted accurate pH measurements over a range of 5.5 units. This is of particular interest to detecting metal ions since, for example, zinc exhibits an approximately 1000 -fold range of concentration in sea water. Moreover, the calibration for an individual sensor will not depend on the length of the fiber, as it will with a ratiometric approach.

Figure 2:
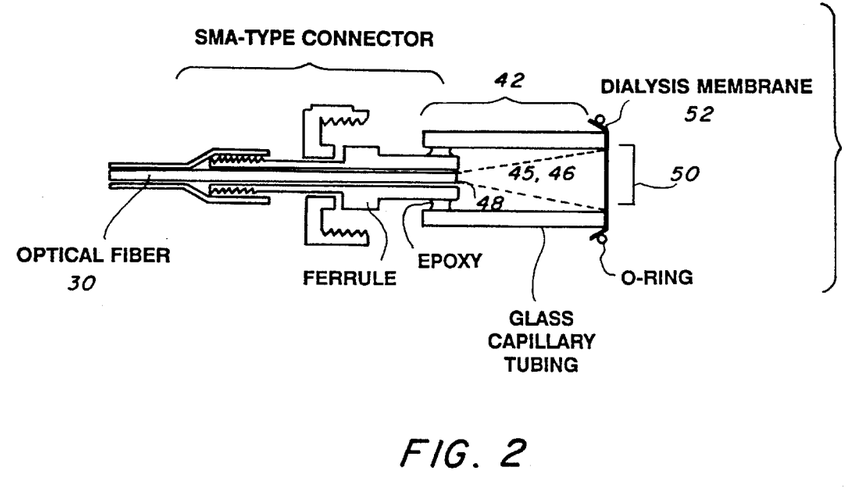
FIG. 2 shows a distal sensing tip for use in a preferred embodiment of the invention.

For remote in situ operation, a distal sensing tip 40 (a typical embodiment is shown in FIG. 2) is employed. In this embodiment, the sensing tip has a housing 42 that defines a chamber 44 that contains the indicator 45 and macromolecule 46. An optical fiber 30 passes through an opening 48 in the housing 42, to permit optical stimulation and photoluminescent monitoring. A second opening 50 in the housing 42 is covered with a semipermeable membrane 52. The membrane permits passage of metal ions, but contains the indicator 45 and macromolecule 46 within the chamber 44.

Alternatively, the macromolecule 46, indicator 45, and the analyte are put in solution together and photoluminescently analyzed in a cuvet.

The criterion for selecting a macromolecule 46 is that the macromolecule selectively complexes with a metal ion species. For example, any of the mammalian carbonic anhydrases in their apoenzyme form (i.e., metal-free form) should exhibit good selectivity for Zn(II). The mammalian carbonic anhydrases that have been tested to date (bovine and Human II) exhibit good selectivity for Zn(II). Moreover, synthetic molecules, such as non-biological polymers, may be synthesized to mimic the chelation site of the mammalian carbonic anhydrases (see J. T. Groves and J. R. Olson, Inorganic Chem. 24 2715-17 (1985)). Likewise, polypeptides, proteins, and polynucleotides are known to be adaptable for selective complexation. Incorporating the functional group:

permits modification of a large number of macromolecules to be selective for zinc. For example, skilled practitioners will recognize that incorporating the active site of carbonic anhydrase, will provide a macromolecule that is selective for zinc.

Figure 10:
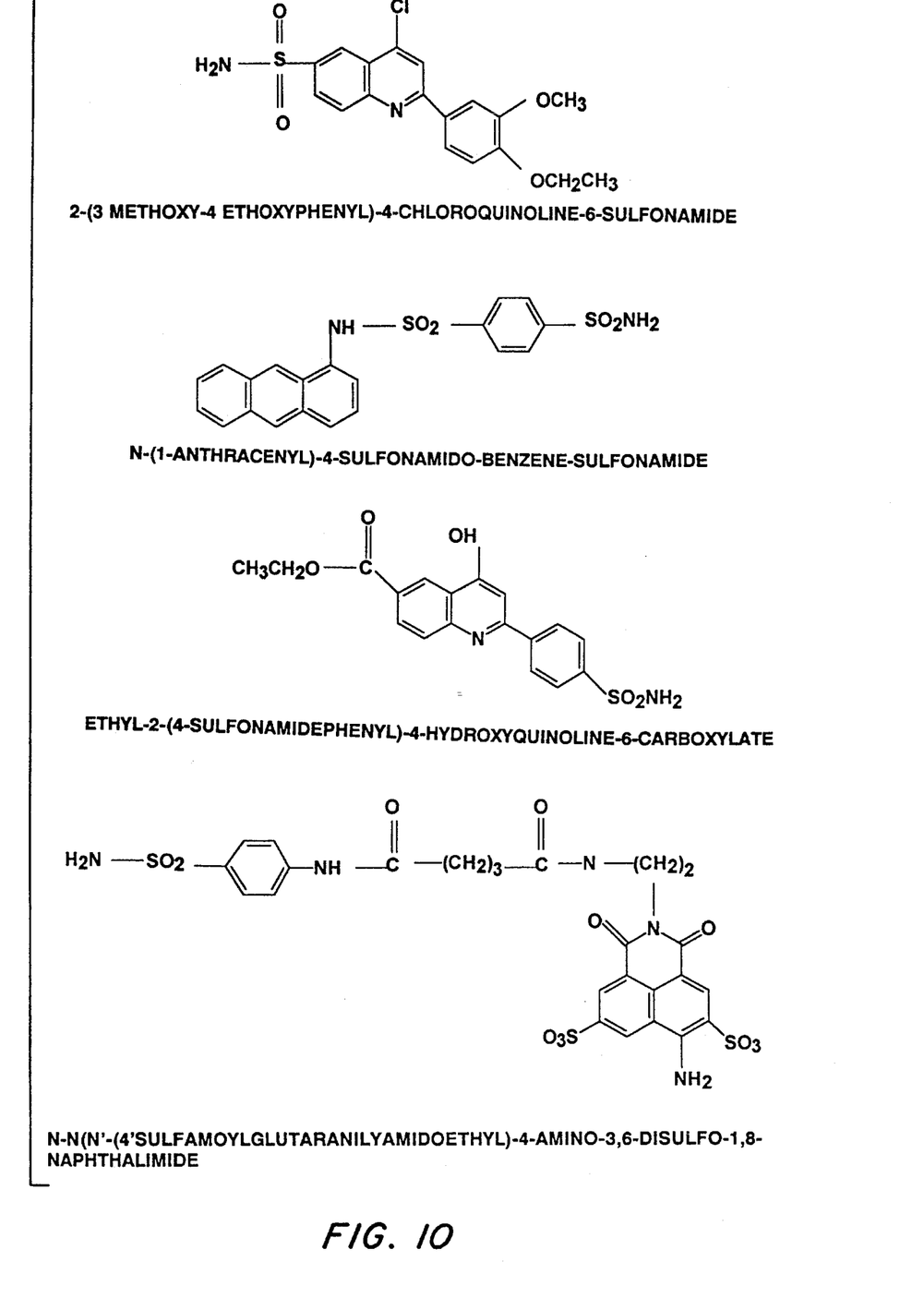
FIG. 10 shows several indicator species for use in the invention.

The criteria for selecting an indicator 45 are (1) that the indicator should exhibit some photoluminescent response in its unbound state (i.e., free in solution, not bound to a metallomacromolecule complex), (2) that the indicator should bind (either at the active site or to some other site) to a complex of the macromolecule and the target metal ion (preferably this binding interaction should have a high equilibrium constant), (3) that the indicator should exhibit some photoluminescent response in its bound state that is measurably different from its photoluminescent response in its unbound state. Suitable indicators include any of the fluorescent aryl sulfonamide that bind as competitive inhibitors to the apoenzyme (or other macromolecule). Typical indicators include dansylamide and hydroxynapthalenesulphonamide. Other appropriate indicators, shown in FIG. 10, include 2-(3-methoxy-4-ethoxyphenyl)-4-chloroquinoline-6-sulfonamide, N-(1-anthracenyl)-4-sulfonamido-benzene-sufonamide, ethyl-2-(4-sulfonamidophenyl) -4-hydroxyquinoline-6-carboxylate,and N-(N' -(4'-sulfamolyglutanilyamidoethyl)-4-amino -3,6-disulfo-1,8-napthalimide.

Having described the invention, the following examples are given to illustrate specific applications of the invention, including the best mode now known to perform the invention. These specific examples are not intended to limit the scope of the invention described in this application.

EXAMPLE 1

Detection of Zn(II) in Aqueous Solution by Measurement of Change to Indicator Fluorescence Lifetime The fiber optic phase fluorometer 20 employed was a modification of the apparatus reported in Thompson et al., *Appl. Spectrosc* 44., 117–22 (1990), and in Golden et al., *Opt. Eng.* 31, 1458–62 (1992), both incorporated by reference in their entirety herein. The fiber optic phase fluorometer 20 was adapted for use with a commercial phase fluorometer (ISS K2, Champaign, Ill.) (Thompson, R. B., Lakowicz, J. R., *Anal. Chem* 65 853–57 (1993)). The apparatus is depicted schematically in FIG. 3.

Figure 3:
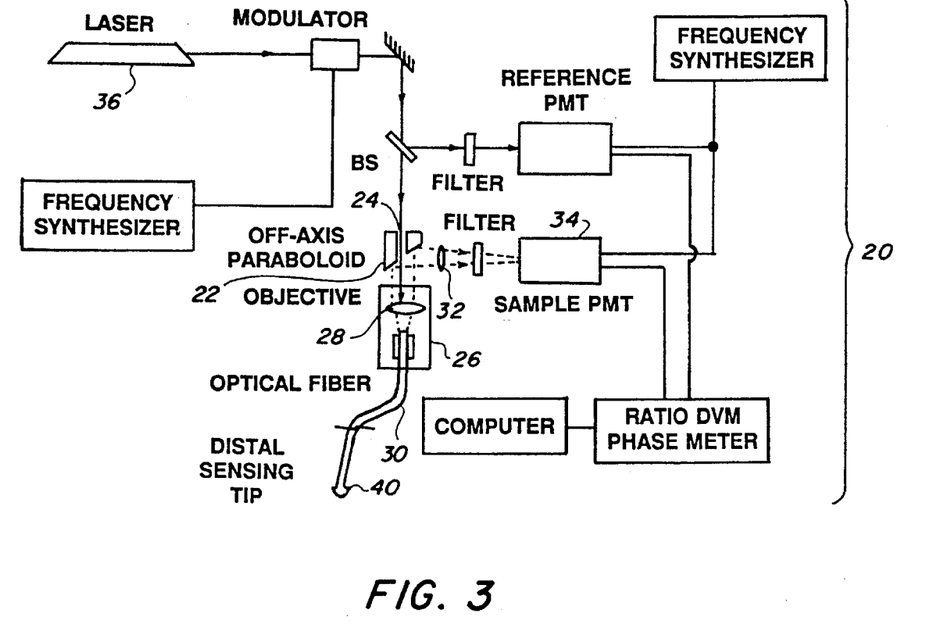
FIG. 3 shows an apparatus for measuring changes in photoluminescent lifetime, according to a preferred embodiment of the invention.

The turret was removed from the sample chamber of the original apparatus, and replaced with a 6×6 in. breadboard, on which was mounted an off-axis parabolic mirror 22 (Janos A8037-105), with a 0.062 in. hole 24 along its mechanical axis, and a precision fiber positioner 26 (Newport-Klingler FP-1015), with its microscope objective replaced with a 25 mm f/1 synthetic fused-silica lens 28 (Newport-Klingler SBX-019). Both positioner 26 and mirror 22 were mounted on small three-axis translators (not shown). The optical fiber 30 (General Fiber Optics Catalog No. 16-200S 200 μm core plastic clad silica, 2–5 m long) was held in the positioner with a fiber holder, a glass capilary tube, or an SMA 905 connector (Amphenol) (not shown). In addition, the emission polarizer holder was removed and replaced with a 75-mm focal length fused silica lens 32 to focus the fluorescence emission on the sample PMT 34 cathode.

Excitation was provided by a Liconix 4114NB helium cadmium laser 36 (326nm, 5 mW cw). For alignment purposes it was convenient to launch a He-Ne laser beam (not shown) back down the fiber 30 into the fluorescence collection optics. Excitation intensity was enhanced by insertion and adjustment of a ¼ wave plate (Karl Lambrecht Chicago, Ill.) (not shown) in the laser beam prior to its pasage thought the beam-splitting polarizer.

Human carbonic anhydrase II was converted to the apo form as previously described in R. B. Thompson and E. R. Jones, "Enzyme-based fiber optic zinc biosensor," *Anal. Chem.* 6–5, 730–4 (1993), and in P. L. Whitney, "Affinity chromatography of carbonic anhydrase," *Anal. Biochem.* 57, 467–476 (1974), both incorporated by reference in their entirety herein.

Carbonic anhydrase from bovine erythrocytes (Sigma C-7500) was stripped of its Zn atom by prolonged dialysis at 4 C. in 50 mM sodium acetate pH 5.4 buffer containing approximately 5 mM 2,6-dipicolinic acid (Aldrich). No attempt was made to differentiate the responses of or purify the isozymes likely to be present in this preparation. Following dialysis into 50 mM Na HEPES pH 7.3, 150 mM sodium sulfate, the enzyme was subjected to affinity chromatography on aminomethylbenzenesulfonamide-derivatized Sepharose 4B resin (Sigma)[29] in the same buffer (see Whitney, P. L., *Anal. Biochem.* 57 467–76 (1974)). This resin binds enzyme which still contains zinc ions, and lets apoenzyme pass through. The unretarded peak coresponding to the apoenzyme exhibits practically no fluorescence enhancement in the blue when added to saturating solutions of dansylamide, suggesting that it is almost entirely zinc free and relatively free of dansylamide-binding impurities.

Other materials were as described in R. B. Thompson et al., supra. Frequency-dependent phase and modulation measurements were made, as previously described in J. R. Lakowicz and I. Gryczynski, "Frequency-domain fluorescence spectroscopy," in *Topics in Fluorescence Spectroscopy Vol.* 1: *Techniques*, (J. R. Lakowicz, ed.) pp. 293–336, Plenum Press, New York, 1991, incorporated by reference in its entirety herein, using an ISS K2 fluorometer with excitation provided by a Liconix 4114NB HeCd laser which produced 5 mW CW (multimode) at 325 nm. Measurements were made at emission wavelengths of 440, 460, 480, 500, 520, and 550 nm using interference bandpass filters (20 nm FWHM) and Rose Bengal as a standard (see R. B. Thompson and E. Gratton, "phase fluorimetric method for determination of standard lifetimes," *Anal. Chem.* 60, 670–4 (1988), incorporated by reference in its entirety herein). Where appropriate, data were fit to two-component models using ISS software.

Figure 6:
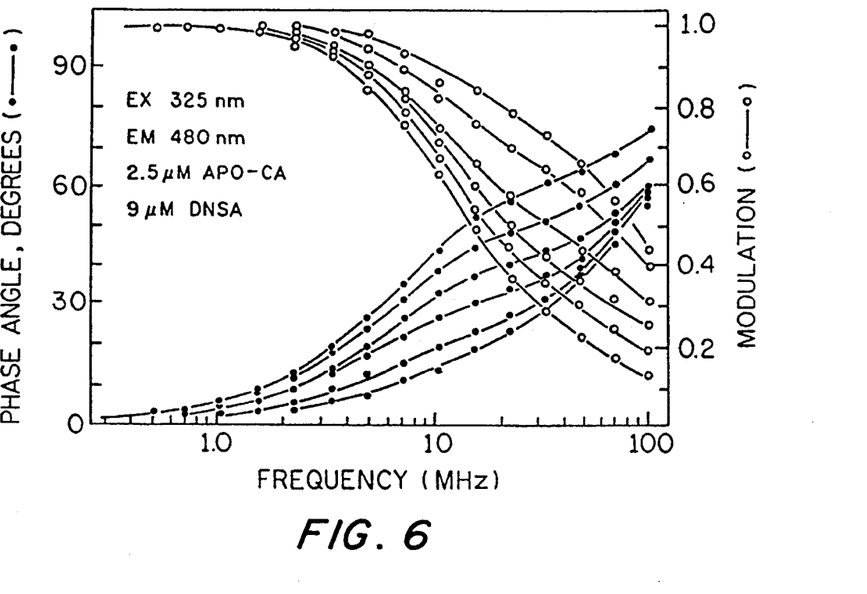
FIG. 6 shows the frequency dependence of phase angle for different zinc concentrations.

Phase shifts and demodulations were measured for 2.5 μM apocarbonic anhydrase, 9 μM dansylamide as a function of zinc concentration at a variety of emission bandpasses. As the zinc concentration increases, one expects to see an increasing fraction of the emission deriving from the long lifetime enzyme-bound form of dansylamide; the concentration of dansylamide is selected to exceed that of the enzyme because the quantum yield of the dansylamide bound to the enzyme is much greater than when it is free in solution and the former contributes disproportionately to the emission. Measurements at 480 nanometers are depicted in FIG. 6. As the Zn concentration increases one does indeed see an increasing fraction of emission from the 20 nanosecond lifetime bound form of the dansylamide, as compared to the 3 nanosecond free form, as indicated by the increased phase shifts and demodulation of emission at particular frequencies with increasing Zn concentration.

Figure 5:
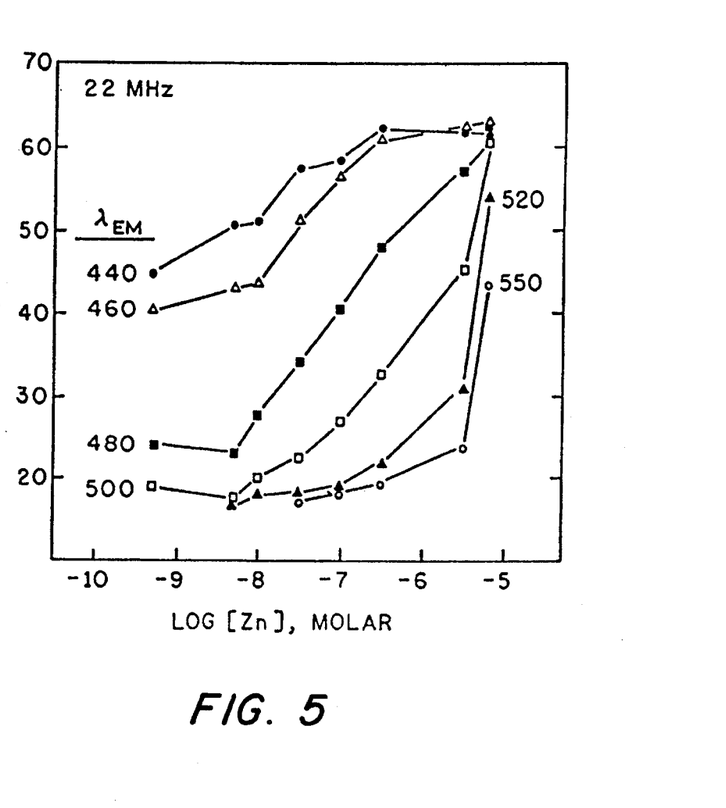
FIG. 5 shows the zinc concentration dependence of measured phase angle in an embodiment of the invention.

It is instructive to plot the measured phase shifts at some suitable frequency as a function of concentration for several emission bandpasses, as done by Szmacinski and Lakowicz ("Optical measurments of pH using fluorescence lifetimes and phase-modulation fluorometry," *Anal. Chem.* 65, 1668–74, 1993). Such a plot (FIG. 5) makes it evident that by judicious choice of emission wavelength zinc concentration can be measured accurately over a greater than 100-fold concentration range. A similar result is obtained if the modulation data are plotted in the same manner. Moreover, the relatively lower precision of the data below nanomolar zinc concentrations and comparison with the data of Szmacinski and Lakowicz suggest that the dynamic range could be extended if, for example, the excitation intensity (<0.2 mW at 325 nm after modulation is imposed) were increased. Note also that curves such as those in FIG. 5 effectively represent calibration curves, and permit accurate determination of zinc levels, even if the emission from one or both forms of dansylamide were not a monoexponential decay.

Figure 7:
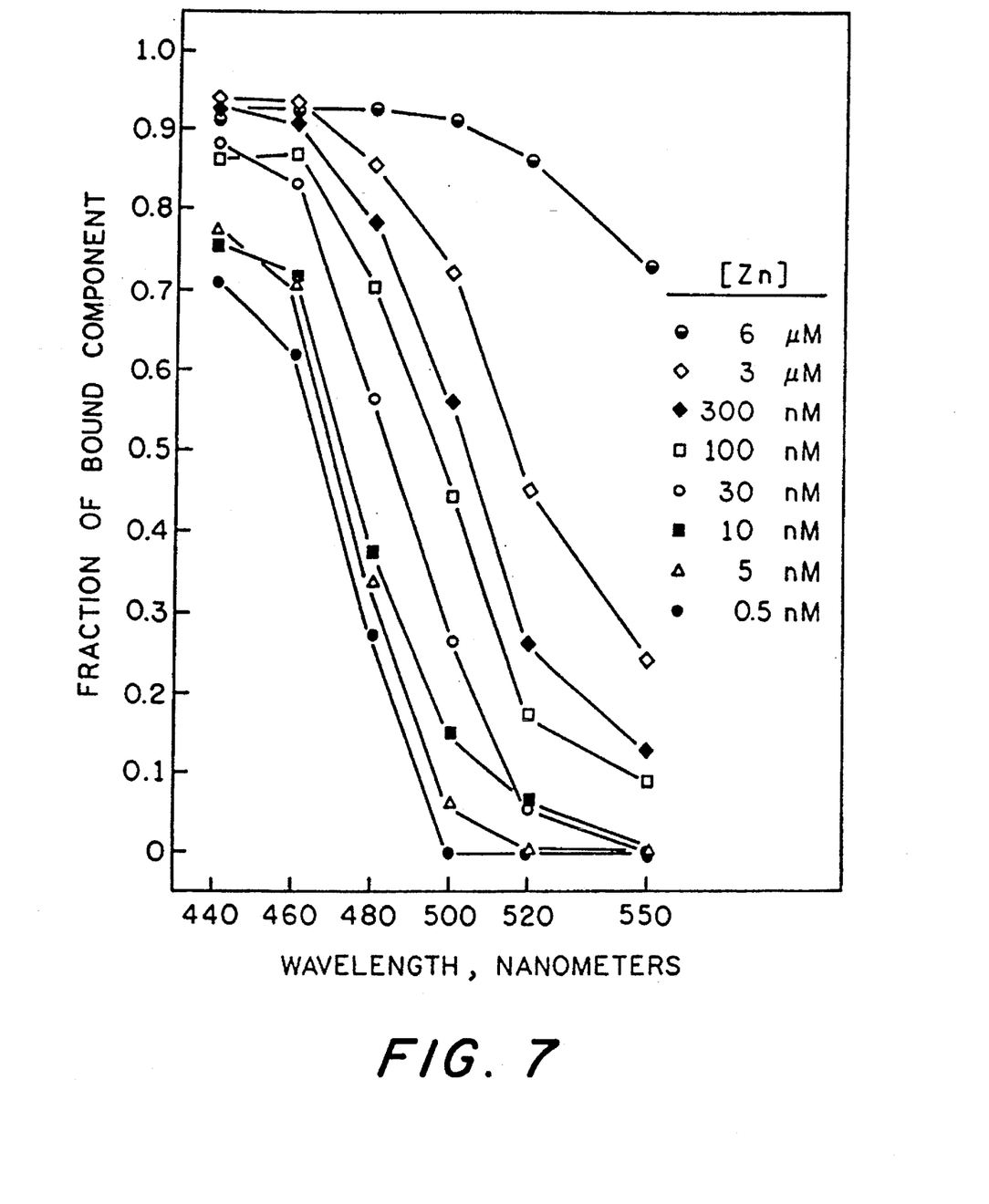
FIG. 7 plots the fraction of bound components versus wavelength for a variety of zinc concentrations in an embodiment of the invention.

If the phase shifts and demodulations measured at different emission wavelengths are fit to a two component model (lines in FIG. 6), the derived fractions of emission corresponding to the bound, long lifetime form may be plotted for different zinc concentrations as a function of emission wavelength (FIG. 7). FIG. 6 shows the frequency-dependent phase shifts and demodulations at 480 n m for 2.5 µM apocarbonic anhydrase, 9 µM for different zinc concentrations; reading phase data upward at 10 MHz, the concentrations are 0.5 nM, 10 nM, 30 nM, 100 nM, 300 nM, and 1 gM zinc. FIG. 7 shows fractions of emission from long-lived (20 nsec) component from 9 µM dansylamide, 2.5 gM apocarbonic anhydrase as a function of wavelength for various concentrations of zinc. As expected, the fraction of apparent emission from the bound form increases both at higher zinc concentrations, and as the emission is observed at the shorter wavelengths where emission from this form predominates. While this procedure uses a much larger data set than the single frequency data in FIG. 5, the results appear generally less satisfactory. This is because the lifetimes of the bound and free forms are not always accurately recovered, while fixing them during the fitting process leads to poorer fits (results not shown). Note also that the typical accuracy and precision of such determinations of fraction of emitters are typically of the order of a few percent, whereas the precision of individual phase and modulation measurements is ordinarily ten-fold better.

The origin of the large dynamic range observed in these systems is at least qualitatively clear: modulation frequencies and emission wavelengths can be chosen such that one form or another contributes disproportionately to the measured phase angle and modulation. In this embodiment, the long lifetime, blue-emitting bound form contributes disproportionately at shorter wavelengths and low modulation frequencies. It was considered worth investigating whether the same dynamic range expansion might not be obtained in the case of emission intensity ratios., by instead of ratioing the intensities at the peaks of the emission of the two forms, one might select other wavelengths where the contribution of one form is much overshadowed by the other. The results of such an experiment are shown for a pH indicator, carboxy-SNARF-6 (see R. P. Haugland, *Handbook of FLuorescent Probes* 1992–1994, Molecular Probes, Eugene, Oreg., 1992). For instance, for measurements of high pH, a wavelength was chosen (530 nm) where nearly all the emission is due to the acid form in order to detect small proportions of it in the presence of large excess of the basic form; the corresponding wavelength for the basic form is 680 nanometers, the "isosbestic point" is 610 nm, and the peaks of the acid and base forms are 550 and 650 nm. Thus it was expected that these three ratios would individually change most rapidly over different pH ranges. The ratios do exhibit different pH dependencies, but only to a modest degree, but the ratio of the peaks seems to cover a broader concentration range. The reason for this is that the ratio of emissions at the peaks (550:650) can vary from 10:1 to 1:10 since the apparent emissivities of the two forms are similar with excitation at 520 nanometers, whereas with the reduced emission at 680 nanometers the basic form can at best only equal the emission at the "isosbestic point", and thus the ratio can only range downward from 1:1. The problem arises in trying to accurately measure intensities differing by greater than ten-fold, when the ordinary accuracy of intensity measurements is seldom better than a few percent. Of course, ratiometric measurements are ordinarily carried out with relatively high precision (nearly 0.1%) due to similar conditions for measurements at both wavelengths, but accurately measuring ratios between 100:1 and 1000:1 might be difficult even in research-grade fluorometers due to the limited dynamic range of the usual PMT detectors at a single gain setting. An approach to this problem might be to incorporate some very accurate and reproducible electronic or optical gain and or excitation level control, such as by the use of a very linear LED excitation source and PIN photodiode detector (see B. W. Smith, B. T. Jones, and J. D. Winefordner, "High-precision fluorimetry with a light-emitting diode source", *Appl. Spectrosc.* 42, 1469–1472, 1988); such a fluorometer has demonstrated precision better than 0.002%. A solid state fluorometer with the precision described by Winefordner should be capable of a 50 dB dynamic range under suitable conditions.

EXAMPLE 2

Detection of Zn(II) in Aqueous Solution by Measurement of Change to Ratio of Indicator Fluorescence Peaks N,N-dimethyl-1-aminonaphthalene-8-sulfonamide (dansylamide) was from Aldrich, HEPES (Ultrapure grade) was from Baker, and other buffer salts were reagent grade or better. Deionized water was further purified by passage through a Millipore system until it exhibited resistance of 18 megohm, and interfering cations were removed from buffers by passage through a bed of chelating resin (Sigma). Following passage through the chelating resin, solutions were stored in clean polyethylene containers and pipetted using plastic pipets or metal-free pipet tips; fluorescence was measured in cuvettes made of synthetic fused silica. Carbonic anhydrase from bovine erythrocytes (Sigma C-7500) was stripped of its Zn atom by prolonged dialysis at 4 C. in 50 mM sodium acetate pH 5.4 buffer containing approximately 5 mM 2,6-dipicolinic acid (Aldrich). No attempt was made to differentiate the responses of or purify the isozymes likely to be present in this preparation. Following dialysis into 50 mM Na HEPES pH 7.3, 150 mM sodium sulfate, the enzyme was subjected to affinity chromatography on aminomethylbenzenesulfonamide-derivatized Sepharose 4B resin (Sigma) (see Lindskog, S. Henderson, L. E., Kannan, K. K., Liljas, A., Nyman, P. O., Strandberg, B. in *The Enzymes*, Vol. 5 (Boyer, P.D., ed.) Academic Press, New York, 1971; pp. 587–665) in the same buffer. This resin binds enzyme which still contains zinc ions, and lets apoenzyme pass through. The unretarded peak corresponding to the apoenzyme exhibits practically no fluorescence enhancement in the blue when added to saturating solutions of dansylamide, suggesting that it is almost entirely zinc free and relatively free of dansylamide-binding impurities.

Figure 4:
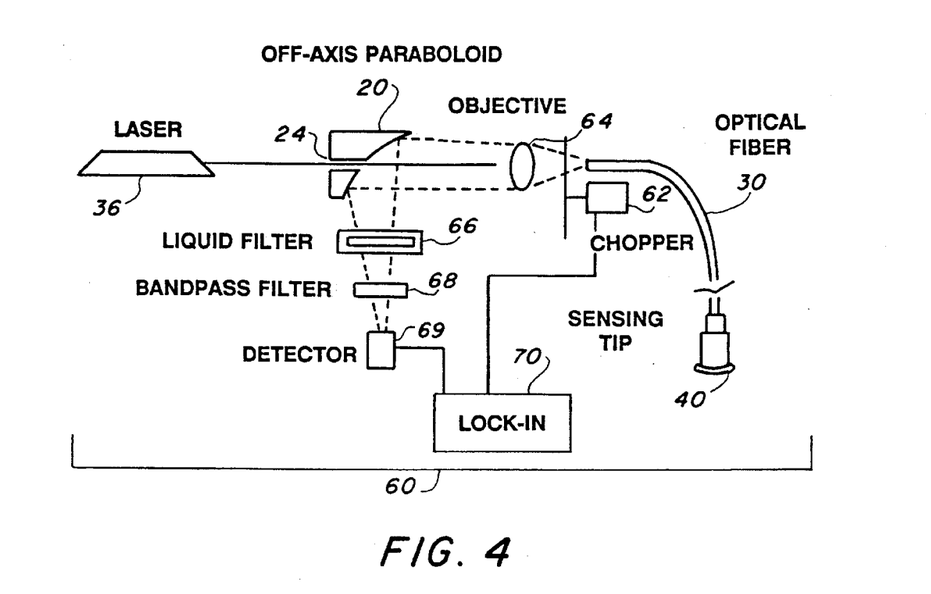
FIG. 4 shows an apparatus for measuring changes in ratios of photoluminescent intensities, according to a preferred embodiment of the invention.

Fluorescence emission spectra and emission intensities in cuvettes were measured on a modified ISS K2 fluorometer 60 (Champaign, Ill.) using a Liconix 4114NB laser 36 emitting approximately 5 mW multimode at 326n m for excitation. The fiber optic sensor optical configuration was similar to the one described supra, and is shown in FIG. 4. Briefly, excitation from the laser 36 passes through a 2 mm hole 24 in the mechanical axis of the off-axis paraboloid 22 (Janos A-8037–205) and is launched into the proximal end of the fiber 30 through a chopper 62 (Stanford Research SR-540) by a 25 mm focal length f/1 fused silica lens 64 (Newport Corp. SBX-019). The excitation passes down the fiber (General Fiber Optics 16–200S 200 μm core plastic clad fused silica step index fiber) and excites the dansylamide at the distal sensing tip 40. The fluorescence passes back down the fiber to its proximal end, where the light spreads out according to the numerical aperture of the fiber; the objective 64 nearly recollimates the fluorescence, which reflects off the off-axis paraboloid 20 and is focused through the filters 66, 68 and onto the detector 69 (a New Focus model 1801 PIN photodiode) whose output at the chopper modulation frequency of 267 H z is amplified and displayed by a Stanford Research SR 510 lock-in amplifier 70. For some measurements through the fiber the off-axis paraboloid, objective lens, and fiber holder were mounted in the ISS fluorometer in place of the cuvette holder, as described elsewhere (Thompson, R. B., Lakowicz, J. R., *Anal. Chem* 65 853–57 (1993)); in these experiments the chopper and lock-in were not used and the DC output of the Hamamatsu R928 photodetector was directly quantitated on the instrument's digital voltmeter after amplification. The off-axis paraboloid and synthetic fused silica objective contribute to background to a negligible extent compared to the photoluminescence of the optical fiber, which is not filtered out by the chopper (see Thompson, R. B., Lakowicz, J. R., *Anal. Chem*, supra); thus the lack of the chopper contributed negligibly to the sensitivity level achieved here. Other fibers tested exhibited greater attenuation, worse photoluminescence, or both. The emission filters were a liquid filter 66 of 2 mm 1M $NaNO_2$ in water closest to the off-axis paraboloid, and an interference filter 68 (Melles Griot) with peak transmission at either 460 or 560 nm to isolate the emissions from the enzyme bound and free forms of the dansylamide, respectively. In practice, the interference filters were rapidly interchanged, and successive measurements ratioed.

Figure 8:
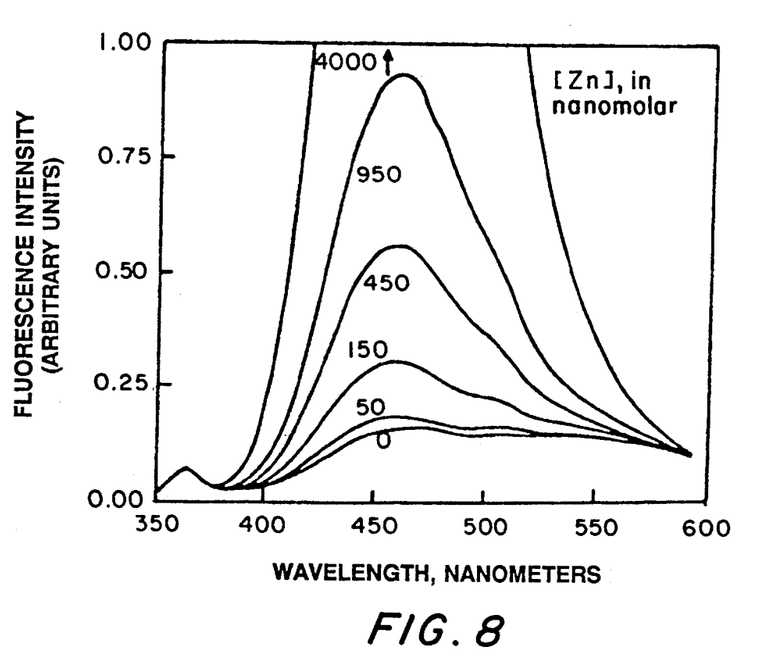
FIG. 8 shows the fluorescence titration curve of carbonic anhydrase and dansylamide with zinc.

The goal of this experiment was to determine zinc in solution by measuring the ratio of fluorescence emission intensities of dansylamide when bound to the carbonic anhydrase (when it is bound to the zinc in the active site) to that of free dansylamide in solution; the fraction of dansylamide bound (and exhibiting strong, blue emission) is determined by the fraction of enzyme active sites containing zinc, and therefore the metal's concentration in solution. Thus for highest sensitivity, it is desirable to detect fluorescence from a few molecules of dansylamide bound to zinc ions in the active site of the enzyme, in the presence of a much greater number free in solution. That this can be done is seen in FIG. 8, which is a titration of 9 micromolar apoenzyme in HEPES buffer in the presence of 9 micromolar dansylamide with low concentrations of zinc. The buffer and enzyme alone exhibited negligible fluorescence, and $ZnCl_2$ concentrations below 100 micromolar did not measurably affect the fluorescence of dansylamide in the absence of enzyme. The fluoresence emission spectrum was measured (excitation at 326nm, 2-mm emission slits) after each successive addition. The fluorescence enhancement observed here by titrating with zinc closely corresponds to the 15-fold enhancement observed by Chen titrating the enzyme with dansylamide (see Chen, R. F., Kernohan, J. C. *J. Biol Chem.* 1967 242, 5813–23.). Furthermore, fluorescence lifetimes of the free and bound dansylamide measured in this laboratory (3.4±0.5 and 20.3±0.2 nsec, respectively, data not shown; see Thompson, R. B., Gratton, E. *Anal. Chem.* 1988 60, 670–674.) matched very closely with the values measured by Chen and Kernohan (3.9 and 22.1 nsec, respectively) twenty-five years previously.

Figure 9:
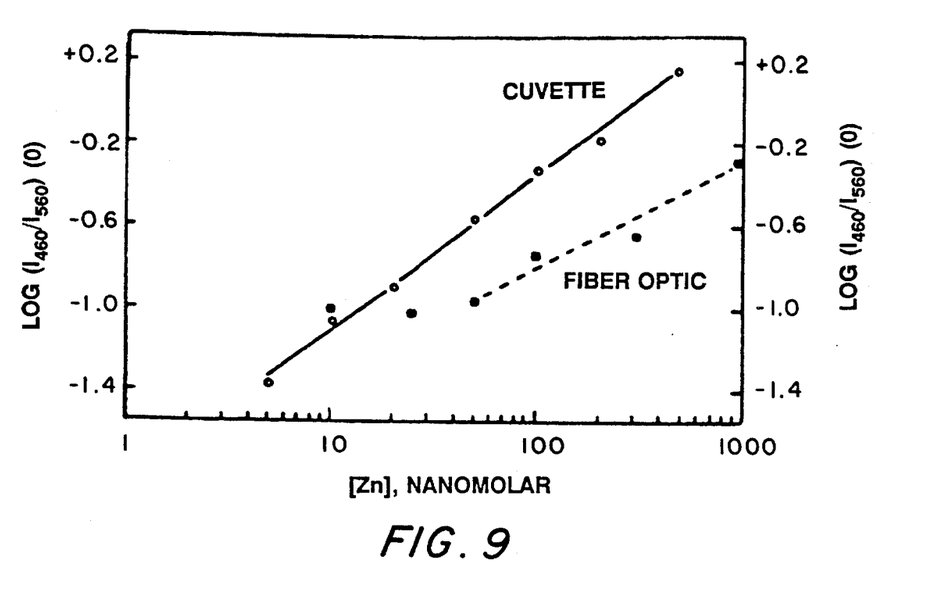
FIG. 9 shows the ratio of fluorescence intensities as a function of zinc concentration.

Data obtained in cuvettes in similar fashion to those in FIG. 8, but with only 1 micromolar apoenzyme and the modest, essentially constant background of intensity due to free dansylamide subtracted from the intensity at 450 nanometers, are plotted as a log-log plot in FIG. 9. Data are shown for titrations like that in FIG. 8, in a cuvette (solid line) and through a fiber (dashed line). The concentration of dansylamide was chosen to be high enough to assure saturation of the binding site when zinc is present there ($K_d$= $2.4\times10^{-7}$ M); the enzyme concentration was chosen to be about ten-fold lower than the dansylamide concentration to assure that at saturation with zinc, the broad emission from the bound form would contribute only modestly at the emission wavelengths of the free dansylamide, and that the intensities would be comparable. Evidently the plot is linear (correlation coefficient =0.9975) over about two decades in concentration. Moreover, the linear range corresponds roughly to the concentration range at which zinc is commonly found in the ocean (see Binland, K. W. *Limnol. Oceanogr.* 1989 34, 269–285, and Sherrell, R. M., Boyle, E. A. *Deep-Sea Res.* 1988 35, 1319–1334.). The enzyme, even in zinc-free form, was stable at 4° C. for more than six months; dansylamide, on the other hand, is not stable for more than a week in dilute solution under these conditions. Taken together, these data suggest that a fiber optic sensor of useful sensitivity can be constructed using carbonic anhydrase/dansylamide in the sensing tip.

The utility of a fiber optic sensor using the above approach was assessed. The ratio of intensities corresponding to the free and bound forms were measured with the apparatus of FIG. 4 by dipping the cleaved end of the fiber into solutions of apoenzyme with dansylamide in HEPES buffer and with zinc ion at varying concentrations. For these experiments intensities were measured through interference filters as described in apparatus; the 460 nm filter was chosen (as opposed to 440 nanometers) to avoid interference from the 441.6 nanometer plasma emission line of the HeCd laser. The results of one such experiment are also depicted in FIG. 9. The most important feature is that the apparent detection limit is at least ten-fold worse than in cuvettes. The principal reason for this is substantial interfering photoluminescence (see Thompson, R. B., in *Topics in Fluorescence Spectroscopy*, Vol. 2: *Principles* (Lakowicz, J. R., ed.) Plenum: New York, 1991: pp. 345–365.) of the optical fiber itself when excited with 326 nanometer light. This photoluminescence contributed to intensities at both 460 and 560 nanometers, and at low zinc concentrations overwhelmed the emission from the bound dansylamide. Other fibers tried exhibited greater photoluminescence, greater attenuation of the excitation, or both. Apart from this the calibration curve appears roughly linear at higher concentrations (correlation coefficient =0.975). Since the optical conditions are not the same (filters versus an emission monochromator), we do not expect the two calibration curves to be identical. Indeed, by judicious choice of wavelengths the most sensitive range may be selected at will.

Obviously, many modifications and variations of the present invention are possible in light of the above teachings. It is therefore to be understood that, within the scope of the appended claims, the invention may be practiced otherwise than as specifically described.

What is claimed is:

1. A method for detecting a selected metal ion species in an analyte medium, comprising the steps of:

disposing a carbonic anhydrase for selective complexation with said metal ion species in said analyte medium;

disposing a photoluminescent indicator species in said analyte medium, wherein said photoluminescent indicator species binds to a complex of said carbonic anhydrase and said metal ion wherein said photoluminescent indicator species exhibits a measurably different photoluminescent response bound to said complex compared to a photoluminescent response exhibited by said photoluminescent indicator species unbound to said complex;

exciting said photoluminescent indicator species with excitation radiation; and monitoring the photoluminescence of said photoluminescent indicator species to detect said measurably different photoluminescent response.

2. The method of claim 1, wherein said photoluminescent indicator species is selected from the group consisting of fluorescent indicators, phosphorescent indicators, and Raman scattering indicators.

3. The method of claim 3, wherein said photoluminescent indicator species is selected from the group consisting of dansylamide, hydroxynapthalenesulphonamide, 2-(3 methoxy-4 -ethoxyphenyl)-4-chloroquinoline-6-sulfonamide, N-(1-anthracenyl)-4-sulfonamido-benzenesulfonamide, ethyl-2-(4-sulfonamidophenyl)-4-hydroxyquinoline-6-carboxylate, and N-(N'-(4'-sulfamoylglutaranilyamidoethyl))-4-amino-3,6-disulfo-1,8-naphthalimide.

4. The method of claim 1, wherein said metal ion species is selected from the group consisting of zinc, cobalt, copper, lead, and nickel.

5. The method of claim 1, wherein said metal ion species is zinc.

6. The method of claim 1, wherein said metal ion species is selected from the group consisting of zinc, cobalt, copper, lead, and nickel, and wherein said photoluminescent indicator species is selected from the group consisting of dansylamide, hydroxynapthalenesulphonamide, 2-(3 methoxy-4-ethoxyphenyl)-4-chloroquinoline-6-sulfonamide, N-(1-anthracenyl) -4-sulfonamido-benzene-sulfonamide, ethyl-2-(4-sulfonamidophenyl)-4-hydroxyquinoline-6-carboxylate, and N-(N'-(4'-sulfamoylglutaranilyamidoethyl))-4-amino-3,6-disulfo-1,8-naphthalimide.

* * * * *